(12) United States Patent
Eriksson et al.

(10) Patent No.: US 6,388,746 B1
(45) Date of Patent: May 14, 2002

(54) METHOD, APPARATUS AND FLOW CELL FOR HIGH-SENSITIVITY DETECTION OF FLUORESCENT MOLECULES

(75) Inventors: Peter Eriksson; Owe Orwar, both of Göteborg (SE); Daniel T. Chiu, Newark, CA (US)

(73) Assignee: Cellectricon AB, Göteborg (SE)

( * ) Notice: Subject to any disclaimer, the term of this patent is extended or adjusted under 35 U.S.C. 154(b) by 0 days.

(21) Appl. No.: 09/634,797

(22) Filed: Aug. 7, 2000

Related U.S. Application Data

(63) Continuation of application No. PCT/SE99/00159, filed on Feb. 5, 1999.

(30) Foreign Application Priority Data

Feb. 6, 1998 (SE) .............................................. 9800360

(51) Int. Cl.⁷ .............................................. G01N 21/64
(52) U.S. Cl. ...................... 356/318; 356/246; 356/317; 250/458.1
(58) Field of Search ............................... 356/317, 246, 356/237, 318, 72, 73; 250/458.1

(56) References Cited

U.S. PATENT DOCUMENTS

| | | | |
|---|---|---|---|
| 3,788,744 A | 1/1974 | Friedman | 356/39 |
| 4,793,705 A | 12/1988 | Shera | 356/318 |
| 4,940,883 A | 7/1990 | Kargen et al. | 219/200 |
| 4,979,824 A | 12/1990 | Mathies et al. | 356/318 |
| 6,049,380 A * | 4/2000 | Goodwin et al. | 356/317 |
| 6,177,277 B1 * | 1/2001 | Soini | 436/63 |
| 6,184,990 B1 * | 2/2001 | Amirkhanian et al. | 356/440 |

OTHER PUBLICATIONS

Lyon, William A. et al., (Confinement and Detection of Single Molecules in Submicrometer Channels) Anal. Chem. vol. 69, pp. 3400–3405 (1997).

"Laser–Induced Fluorescence Detection of Single Molecule in a Capillary", Yuan–Hsiang Lee et al., Analytical Chemistry, vol. 66, pp. 4142 to 4149 (1994).

* cited by examiner

*Primary Examiner*—Frank G. Font
*Assistant Examiner*—Layla Lauchman
(74) *Attorney, Agent, or Firm*—Burns, Doane, Swecker & Mathis, L.L.P.

(57) ABSTRACT

Method and apparatus for high-sensitivity fluorescence detection wherein (I) a sample comprising fluorescent molecules is made to flow through a channel structure (1) comprising a constricted region (2) with a dimension corresponding to the size of a tightly focused laser spot and with extremely thin, transparent walls, (II) a laser beam (3) is focused inside the constricted (2) and thus exciting molecules passing through the constricted region (2), and (III) the fluorescence emitted due to excitation is detected. This enables direct determination of the concentration of a sample without use of internal or external standards. A method for the production of a flow cell for use in said method or apparatus, wherein a part of a channel structure (1) is heated until its melting point is reached, followed by pulling of the structure to lengthen the melted region and make it thinner until it has a dimension corresponding to the size of a tightly focused laser spot at the diffraction limit.

38 Claims, 13 Drawing Sheets

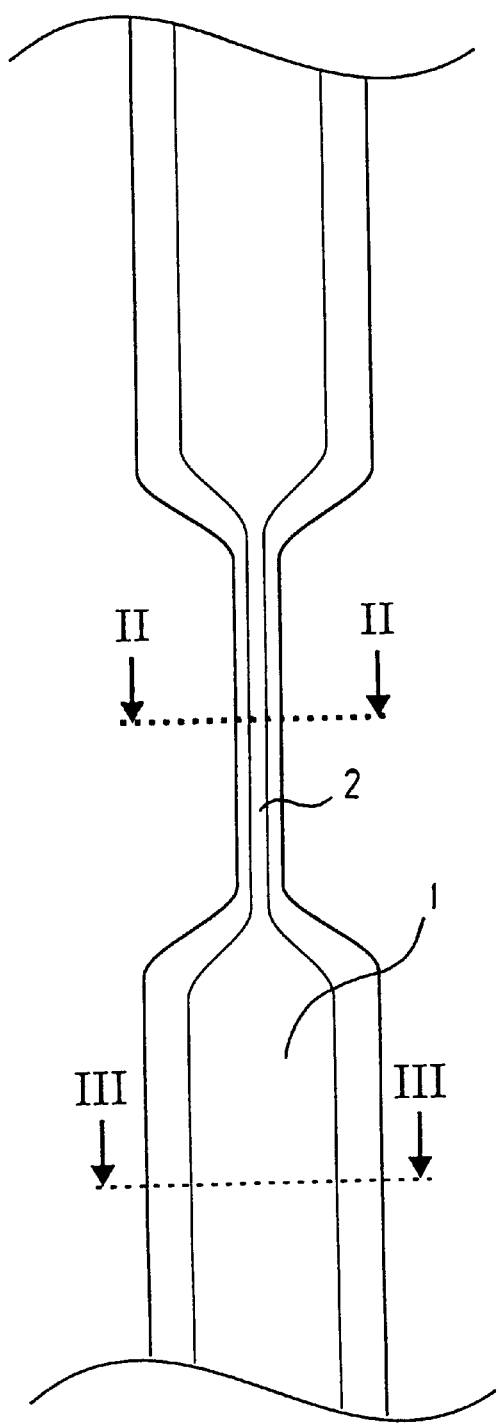
Fig. 1
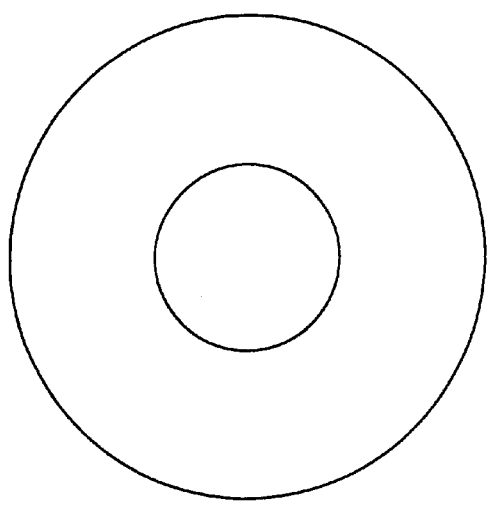
Fig. 2
Fig. 3

76 μm/cm

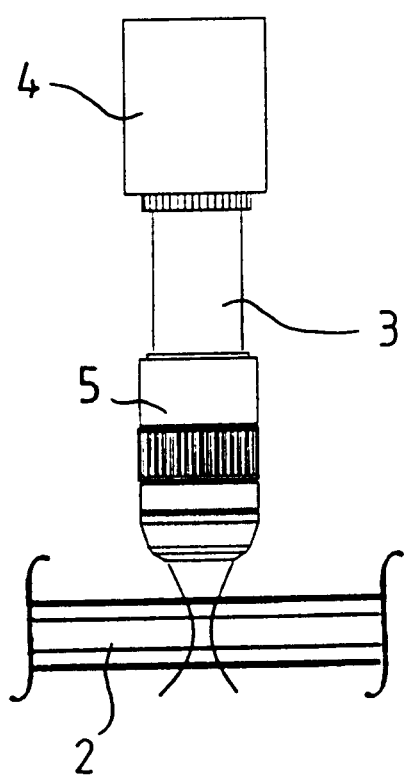
Fig. 9
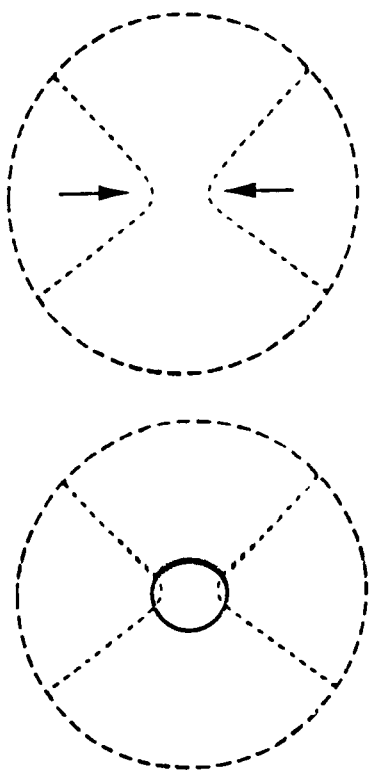
Fig. 10
Fig. 11

METHOD, APPARATUS AND FLOW CELL FOR HIGH-SENSITIVITY DETECTION OF FLUORESCENT MOLECULES

This is a continuation of International Application No. PCT/SE99/00159, filed Feb. 5, 1999, that designates the United States of America and which claims priority for Swedish Application No. 9800360-1, filed Feb. 6, 1998.

TECHNICAL FIELD OF THE INVENTION

The present invention relates to an optical method for high-sensitivity detection of fluorescent molecules based on the use of a highly focused light beam and light-induced fluorescence spectroscopy, to an apparatus for high-sensitivity detection of fluorescent molecules comprising a light source and a fluorescence detector, to a method for the production of a flow cell for high-sensitivity detection of fluorescent molecules, as well as to use of said method, apparatus or flow cell in combination with a microscope.

BACKGROUND ART

Techniques based on miniaturised chemical separation have made possible the analysis of the contents of individual cells (O. Orwar, H. A. Fishman, N. Ziv, R. H. Scheller, R. N. Zare, *Anal. Chem.*, 67, 4261 (1995)), and individual sub-cellular organelles (D. T. Chiu, S. J. Lillard, R. H. Scheller, R. N. Zare, S. E. Rodriguez-Cruz, E. R. Williams, O. Orwar, M. Sandberg, J. A. Lundqvist, Science in press). However, there is a need to analyse the contents of ever smaller sample volumes and even monomeric units cleaved off from single biopolymers such as RNAs, DNAs, and proteins. In order to render this possible, it is necessary to develop techniques with sensitivities approaching the inverse of Avogadro's constant, $N_A$ ($6.0221 \times 10^{23}$ mol$^{-1}$)

The use of microcolumn separation techniques, such as capillary electrophoresis, capillary electrochromatography, and microcolumn high performance liquid chromatography, for the compositional analysis of various types of samples, especially in the area of biomedical research and in the pharmaceutical industry, has experienced tremendous growth during the last twenty years. Since these techniques are particularly useful for the analysis of ultra-small sample volumes, $10^{-6}$ to $10^{-21}$ litres, that often contain trace amounts of analytes, severe demands are placed on detection sensitivity.

The possibility to detect very small quantities of biologically important molecules is of great interest in many fields, such as molecular biology, medical diagnosis, drug development and forensic analysis. Of particular interest is often the detection of antibodies, antigens, hormones, enzymes, proteins, peptides, amino acids or nucleic acids present in a sample. However, these samples often contain very small amounts of the molecules in question and they are therefore difficult to detect adequately. It is often necessary to amplify the material to obtain greater quantities before detection. In the case of e,g. DNA, this amplification is most frequently made by means of polymerase chain reaction (PCR), which duplicates DNA sequence of interest However, amplification of the molecules to be detected is not always desirable since it may, for example, lead to the introduction of substances contaminating the sample. Hence, there is a demand for techniques enabling direct detection of small amounts of a given substance. There are already some techniques available, and most of these are based on optical detection methods and on the use of different spectroscopy methods.

In 1961 came the first report on single-molecule studies in solution (B. Rotman, *Proc. Natl. Acad. Sci., USA*, 47,1981 (1961)). This study also has biological significance since the presence of a single enzyme molecule could be detected using a fluorogenic substrate. In 1976 a single antibody tagged with 80–100 fluorescein molecules could be detected using evanescent-wave excitation (T. Hirschfeld, *Appl. Opt.* 15, 2965 (1976)). Since then, much has been done in this field. One of the most promising techniques for sensitive detection is laser-induced fluorescence, mainly applied in two different set-ups: detection within a focused laser beam and detection in a near-field scanning optical microscope. Other techniques, such as nuclear magnetic resonance, electrochemistry, cavity ring-down spectroscopy have also been proposed for single molecule studies. Also, the use of biosensors in chemical separations have made it possible to distinguish single biomolecules (O. Orwar, K. Jardemark, I. Jacobson, A. Moscho, H. A. Fishman, R. H. Scheller, R. N. Zare, *Science*, 272, 1779 (1998)).

Methods based on laser-induced fluorescence have been demonstrated to have the ability to detect a single fluorescent molecule in solution. However, the known methods are diffusion-limited and can be employed only for samples containing a large amount of fluorescent molecules. Therefore, the sampling efficiency, i.e. the number of fluorescent molecules detected over the total amount of fluorescent molecules present in the solution, is extremely small, on the order of $10^{-6}$ or even less. In one commonly employed embodiment of single-molecule detection in solution, a drop containing the fluorescent molecules is placed on a coverslip (S. Nie, D. T. Chiu, R. N. Zare, *Anal. Chem.*, 67, 2849 (1995) and R. Riegler, U. Mets, J. Widengren, P. Kask, Eur. Biophys. J., 22, 169 (1993) and S. Nie, D. T. Chiu, R. N. Zare, *Science*, 266, 1018 (1994)). Single-molecule fluorescence is then collected and detected in a confocal fluorescence microscope set-up. With this technique it is, however, difficult to accomplish detection of molecules separated by a microchemical fractionation technique.

Detection of single molecules has also been achieved in capillary structures, both coupled to separation devices and as stand-alone flow cells (Y-H Lee, R. G. Maus, B. W. Smith, J. D. Winefordner, *Anal. Chem.*, 64, 4142 (1994)). Also in these cases, however, detection has been performed in solutions containing a large excess of the fluorescent molecule over the actual detected number of molecules. Typically, $10^{-9}$ to $10^{-12}$ M of fluorescent solutes are introduced into the system in solution volumes of from $10^{-6}$ to $10^{-3}$ l. Thus, again sampling efficiencies on the order of $10^{-6}$ to $10^{-12}$ are obtained.

In the last decade, there has been rapid development in high-resolution optical and electro-optical techniques, driven by the need to understand biochemical and biophysical processes in greater detail. For example, confocal microscopy and two-photon microscopy have provided striking images on the workings of cellular machinery, such as the dynamics of intracellular calcium ion and the localisation of single serotonin-containing granulae in RBL cells (see egg. B J. Bacskai, P. Wallen, V. Lev-Ram, S. Grillner, R. Y. Tsien, *Neuron*, 14, 19–28 (1995) and S. Maiti, J. B. Shear, R. M. Williams, W. R Zipfel, W. W. Webb, *Science*, 275, 530–532 (1997)). Higher optical resolutions—as high as 12 nm—are obtained in near-field spectroscopic probes, wherein it is possible to reach, or even bypass the Abbe diffraction limit (E. Betzig, J. K. Trautman, T. D Harris, J. S. weiner, R. L Kostelak, *Science*, 251, 1468 (1991)). The manipulation of single organelles and even single biomolecules has been made possible by optical trapping, and this technique has been applied to a wide range of interesting biological problems (A. Ashkin, *Phys. Rev. Lett.*, 24 (4), 156 (1970) and K. Svoboda, S. M. Block, *J. Annu. Rev. Biophys. Biomol. Struct.*, 23, 247–285 (1994) and D. T. Chiu, A. Hsiao, A. Gaggar. R. A. Garza-Lopez, O. Orwar, R. N. Zare, *Anal. Chem.*, 69, 1801–1807 (1997)).

As stated above, techniques that can detect a single molecule rapidly moving in solution are based almost exclusively on optical methods. By using lasers which produce spatially and temporally coherent bundles of monochromatic light, a tightly focused diffraction-limited laser spot can be obtained with appropriate optics.

If detection is made through a pinhole or a narrow slit, in a confocal detection arrangement, an extremely small laser probe volume can be created on the order of about $5 \times 10^{-16}$ 1. In this way, an extremely narrow depth-of-focus is obtained. The confocal advantage includes extremely low background scattering from Rayleigh and Raman events, where the intensity has an inverse quadruplicate dependence on laser wavelength, a linear dependence on laser power, and is unsaturable. Molecular fluorescence on the other hand, is saturable and its dependence on laser irradiance is exponential. Using confocal fluorescence microscopy, it has been demonstrated that single highly fluorescent molecules such as laser dyes can be detected with high signal-to-noise ratios (S. Nie, D. T. Chiu, R. N. Zare, *Anal. Chem.*, 67, 2849 (1995) and R. Riegler, U. Mets, J. Widengren, P. Kask, *Eur. Biophys. J.*, 22, 169 (1993) and S. Nie, D. T. Chiu, R. N. Zare, *Science*, 266, 1018 (1994)). However, also according to this technique, high concentrations of the molecules to be detected are necessary. The sample containing the molecules to be detected is placed in a chamber or on a coverslip and detection of a single molecule is therefore diffusion limited. In this random and chaotic detection format, there exists no externally applied force to place the molecules in the laser probe volume. This means that the sampling efficiency, defined as the number of detected molecules over the total number of molecules present in the sample, typically is on the order of $10^{-6}$ or less. To fulfil the criteria of volume-independent detection limits approaching $N_A^{-1}$, this ratio needs to be close to unity. If this criteria is fulfilled it is possible to detect and probe a molecule even if the sample solution only contains a single molecule.

Reports on experiments using laser-induced fluorescence detection in capillaries have demonstrated exquisite sensitivities (Y-H Lee, R. G. Maus, B. W. Smith, J. D. Winefordner, *Anal. Chem.*, 64, 4142 (1994) However, the instrumentation and analysis (deconvolution algorithms) have seen difficult to implement in some cases and most of the techniques does not have the desired concentration detection limits since the probe volume is much smaller than the dimensions of the capillaries Although a single molecule can be detected once it resides in the probe volume, most molecules do not traverse the probe volume and are thus missed.

SUMMARY OF THE INVENTION

The object of the present invention is to provide a simple method and apparatus that enables high-sensitivity detection of fluorescent molecules, and in particular ultra-sensitivity detection of single fluorescent molecules in a flowing stream, said detection having a sampling efficiency close to unity. This means that it will be possible to detect a single molecule present in a solution regardless of the volume of the solution.

Thus, the present invention relates to an optical method for high-sensitivity detection of fluorescent molecules based on the use of a highly focused light beam and light-induced fluorescence spectroscopy characterised in that (I) a sample comprising at least one fluorescent molecule is made to flow through at least one flow cell consisting of at least one channel structure comprising at least one constricted region, said at least one constricted region having a cross-section of a dimension corresponding to the size of a tightly focused light spot close to or at the diffraction limit and extremely thin, transparent walls, (II) at least one light beam is focused close to or at the diffraction limit inside said at least one constricted region and thus exciting any fluorescent molecules present in the sample volume passing through said at least one constricted region, and (III) the fluorescence emitted when a fluorescent molecule or a group of molecules passes through said at least one constricted region and is excited is detected.

The invention also relates to an apparatus for high-sensitivity detection of fluorescent molecules comprising at least one light source and at least one fluorescence detector, characterised in that it further comprises at least one flow cell consisting of at least one channel structure comprising at least one constricted region, said at least one constricted region having a cross-section of a dimension corresponding to the size of a tightly focused light spot close to or at the diffraction limit and extremely thin, transparent walls, said at least one channel structure being adapted to accommodate the sample comprising the molecule or molecules to be detected.

Furthermore, the invention relates to a method for the production of a flow cell for use in high-sensitivity detection of fluorescent molecules characterised in that a channel structure is obtained at an appropriate method, and at least one region of said channel structure is then heated until the melting point of the material constituting the channel structure is reached, and in that the channel structure finally is pulled in order to lengthen the melted region and thus make it thinner until it has a dimension corresponding to the size of a tightly focused laser spot close to or at the diffraction limit, said material constituting the channel structure being transparent or turning transparent during the heat treatment.

Finally, the invention relates to use of the above mentioned method and/or apparatus for high-sensitivity detection of fluorescent molecules, and/or a flow cell produced according to the above mentioned method in combination with a microscope, preferably a confocal fluorescence microscope, and most preferably a scanning confocal fluorescence microscope.

The characterising features of the invention will be evident from the following description and the appended claims.

According to the present invention, it is thus possible to detect single fluorescent molecules, as well as groups of fluorescent molecules. However, it is also possible to detect non-fluorescent molecules by tagging them with a fluorescent or a fluorogenic compound before detection, Beside detection of fluorescent molecules, it is also possible according to the invention to detect small fluorescent particles.

The light beam used according to the invention preferably has a wavelength of approximately 200–1500 nm. The light source is preferably a laser, and most preferably an argon ion laser.

It is possible to use more than one light source, and it is then advantageously if each light source emits light at a different wavelength. This enables simultaneous detection of molecules with different fluorescence spectral properties.

The light beam is focused to a spot close to or at the diffraction limit in the constricted region of the flow cell through use of appropriate means. Said means may e.g. be a high-numerical aperture microscope objective (100×).

The excitation of the fluorescent molecules may be achieved either by a single-photon process or by a multi-photon process. Preferably, the excitation is made in a two-photon or multi-photon mode.

The channel structure used according to the present invention is preferably a capillary, and most preferably a fused silica glass capillary. It may also be a channel etched into a chip. Furthermore, it is advantageously to use several channel structures parallelly. The channel structures are then preferably arranged in a co-planar mode. This feature is advantageous especially for high throughput screening applications.

The flow channel may further form an integrated and continuous part of a glow injection analysis system or a separation system, such as a system for capillary electrophoresis, capillary electrochromatography, liquid chromatography or gas chromatography. For these purposes the flow channel may be packed with a suitable material, such as beads.

The dimensions of the constricted region of the flow cell according to the invention is made to match the size of the volume being illuminated by the light. The constricted region preferably has an inner diameter (id.) of approximately 0.2–8$\mu$m, and an outer diameter (o.d.) of approximately 0.4–40$\mu$m. Since the constricted region of the flow cell is physically narrower than the rest of the flow cell, the solution cravelling through the flow cell is focused in the constricted region. Since only a small portion of the flow cell is constricted, the flow cell can accommodate large sample volumes. This possibility to handle large sample volumes is an important and distinctive feature of the present invention. The concentration sensitivity is several orders of magnitude higher than previous accounts of single molecule detection. It is possible to detect a single molecule almost independent of the sample volume in e.g. a flow injection analysis scheme. Since many biological samples are concentration limited rather than volume limited, this aspect of the invention is important. Once the sample is introduced in the flow cell, the probability of detecting the molecules is almost unity since the dimensions of the probe volume and the constricted region are well matched, and all molecules will traverse the probe volume with knowledge of the total sample volume injected into the flow cell, this can yield sample concentration without calibration. This is also an important and distinctive feature of the present invention because it abolishes the need to detect analytes in standard solutions of known concentrations. Hence, quantitative analyses can be performed at lower cost and higher sample turnover rate than conventional technologies.

In order to maintain the quality of the light beam and to minimise spherical and other aberrations, the channel walls are made extremely thin, on the order of a few microns or less. These thin walls minimise the cylindrical lensing effects observed for capillaries with walls of regular thicknesses.

It is advantageously to place the constricted region in a medium with a refractive index close to that of the material constituting said constricted region This medium is preferably oil or water, or water supplemented with appropriate additives This results in a higher optical tuning of the system, by avoiding the light passing through a medium with a refractive index of 1.

Furthermore, it is advantageously that the channel structure comprises more than one constricted region. It is then possible to measure the emitted fluorescence at different constricted regions and cross-correlate the data in order to improve the probability of identifying a true detection event from a chaotic background event.

The detection of the emitted fluorescence is preferably made by means of a highly sensitive photon detector, such as a single photon counting diode or a photon counting photomultiplier tube, or a highly sensitive photon counting charge coupled device., a VIM camera or a streak camera. It is possible to perform the detection either at a single wavelength or in a multicolour format. It is further possible to perform the detection in either a confocal or a non-confocal mode. The confocal mode is preferred for single-photon excitation and the non-confocal mode is preferred for multi-photon excitation.

The flow cell used according to the invention forms preferably an integrated and continuous part of a flow injection analysis system or a separation system, such as a capillary electrophoresis, capillary electrochromatography, liquid chromatography, or gas chromatography system.

A particularly interesting field for application of the present invention is analysis of single DNA, RNA, and protein molecules by sequential cleavage and detection of the fluorescently labelled monomeric units. In principle, the methodology can be applied for such analyses where the biomolecules of interest have been extracted from a single cell or even a single organelle.

Because most biologically relevant molecules do not contain any features for their sensitive detection in fluorescence, they need to be modified chemically to become fluorescent Highly selective reagents that renders biomolecules fluorescent are available (see e.g. Handbook of Molecular Probes and Research Chemicals sixth edition, 1996, by Richard P. Haugland). These fluorescent or fluorogenic reagents can be of a high specificity and react only with a single molecule, for example, fluorescently labelled antibodies or they can be general in nature and react with specific functional groups present in many different types of molecules. Examples of the latter include aldehydic reagents (e.g. o-ophthalaldehyde, and 2,3-naphthalenedicarboxaldehyde) for amino acids, and peptides that in the presence of nucleophilic co-reagents such as cyanide ion or β-mercaptoethanol form highly fluorescent isoindolyl derivatives, and bimanes (e.g. monobromobimane, and monochlorobimane) that form highly fluorescent derivatives upon conjugation with thiol-containing molecules.

There are many different ways in which analytes of interest can be converted into fluorescent derivatives. It is, for example, possible to react them with a fluorescent or fluorogenic reagent prior to introduction of the sample into the capillary flow cell. It is also possible to react the analytes with a fluorogenic compound on-column, i.e. within the flow cell. This can be achieved simply by filling the capillary with the fluorogenic reagent of choice, and because the reagent does not fluoresce in itself, this procedure does ideally, not cause any interference. This procedure of analyte derivatisation has been successfully adopted to the analysis of single atrial gland vesicles isolated from the mollusc *Aplysia Californica* (D. T. Chiu, S. J. Lillard, R. H. Scheller, R. N. Zare, S. E. Rodriguez-Cruz, E. R. Williams, O. Orwar, M. Sandberg, J. A. Lundqvist, Science in press). In the case of single-cell analysis, the fluorescent or fluorogenic reagent can be either microinjected or electroporated directly into a biological cell before it is lysed and introduced into the capillary. It is also possible to modify the flow cell in such a way that it can accommodate a biological cell in a compartment or reaction chamber that has been injected into said flow cell. Such a biological cell reaction chamber can, for example, be formed by two constrictions in the capillary where the distance between the constrictions is matched to accommodate a single biological cell. It is also feasible to connect capillaries or electrodes to the cell reactor for chemical manipulation and electroporation of the content of the biological cell.

Because of the following unique properties of the present invention;

1. Single-molecule detection capabilities
2. Calibration-free analysis
3. Extremely high concentration sensitivity
4. Compatible to separation techniques
5. Enclosed system it can be applied to a wide range of diagnostic and analytical applications, for which current technologies are impossible or extremely difficult to implement. Examples of such applications given below are just some examples, and does not limit the applicability of the present invention. These applications include measurement of single bacterial or viral particles in body fluids, or dietary products, and determination of the contents of single cells. In the forensic sciences it can be used for identifying DNA extracted from single cells In situations where e.g. blood has been mixed or pooled from several individuals, this represents a tremendous advantage over the use of the polymerase chain reaction (PCR), which is difficult to implement in such situations. In the area of bedside patient surveillance it might be used to measure inflammatory response proteins, indicators of intra-vasal chock, prechock indicators, and coagulation proteins etceteras.

The technology can also be used for determination of indicators of myocardial infarction, cardiac enzymes, etcet-eras. In clinical diagnostics, it can also be used for determination of DNA, RNA, bacteria, viruses, and immunoglobulins etceteras. It can further be used for detection and quantitation of immunoglobulin titers in patient serum, HIV, hepatitis, borrelia, and autoimmune markers. The present invention can also be used in the area of process analytical chemistry for quality control and product assurance, in particular of pharmaceutical formulations. It might also be well-suited for drug screening purposes including high throughput screening in a multiplexed format.

BRIEF DESCRIPTION OF THE DRAWINGS

The invention will now be described in further detail hereinafter with reference to the accompanying drawings on which;

FIG. 1 is a schematic illustration of a flow cell for use according to the invention.

FIG. 2 is a cross-sectional view of the constricted region of the flow cell shown in FIG. 1 along the line II—II.

FIG. 3 is a cross-sectional view of the channel structure of the flow cell shown in FIG. 1 along the line III—III. It also illustrates the differences between the dimension 0f the channel structure and the dimension of the constricted region shown in FIG. 2.

FIG. 9 illustrated illumination of the constricted region of a flow cell according to the invention by means of a laser.

FIG. 10 shows a cross sectional view of an idealised laser beam brought to the limit of diffraction.

FIG. 11 shows the preferred embodiment of the invention where the inner diameter of the separation channel, which is shown in a cross sectional view, matches the size of the focused laser spot.

DESCRIPTION OF PREFERRED EMBODIMENTS OF THE INVENTION

The heart of the system used according to the invention is the specially designed flow cell comprising at least one constricted region. This flow cell is preferably made of a fused silica capillary. A schematic illustration of a flow cell according to the invention is shown in FIG. 1. The flow cell in FIG. 1 consists of a channel structure 1 with a constricted region 2. For comparison of the dimensions of the different parts of the flow cell, a cross-section of the constricted region of the flow cell in FIG. 1 along the line II—II is shown in FIG. 2, and a cross-section of the non-constricted region of the flow cell in FIG. 1 along the line III—III is shown in FIG. 3 The constricted region can be located at any position along the capillary. The inner diameter of the constricted portion is made to match the size of a tightly focused laser beam, preferentially a diffraction limited spot. The outer walls are made as thin as possible to minimise distorting cylindrical lensing effects. The ratio between the inner diameter and the outer diameter should not exceed a factor of five, and preferentially be between 1.5 and 5.

The flow cells used according to the present invention can e.g. be fabricated from fused silica capillaries. Other types of channels can also be used. Fused silica capillaries are commercially available from several vendors. If commercial capillaries are used as starting material in the production of the flow cell according to the invention, it is advantageously to use a capillary with relatively small outer diameter and small inner diameter in order to facilitate the formation of constricted regions of sufficient small dimensions to become useful for high-sensitivity fluorescence detection. However, it is the ratio of the inner diameter between the non-constricted region of the capillary and the constricted region of the capillary, that together with the length of the capillary dictates how large sample volumes that can be accommodated by the flow cell. Thus, for achieving the highest concentration sensitivity, a large ratio between the diameters of the non-constricted and the constricted regions are preferable, together with flow cells of Long length. Typically, capillaries with about 20–600 $\mu$m outer diameter, and about 5–100 $\mu$m inner diameter are suitable as starting material in the production of flow cells according to the invention. The length of the capillaries used may vary depending on application; typically the length is between 20 cm and 100 cm.

Figure 4:
FIG. 4 is a longitudinal view of the constricted region of the capillary in FIG. 2.
Figure 5:
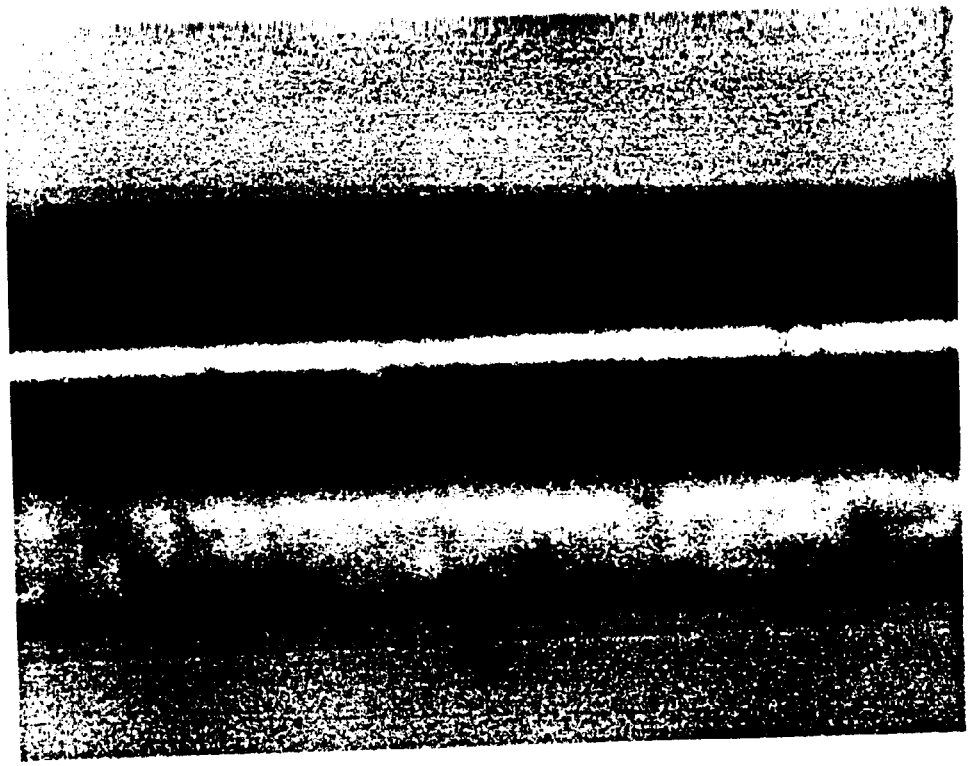
FIG. 5 shows the non-constricted a fused silica capillary according to the invention in a longitudinal sectional view.

The constricted region is formed by heating a small section, typically less than 5 mm of the capillary, e.g. by use of a flame, such as a butane/oxygen torch burner. When the melting temperature of the fused silica glass is reached, the capillary is pulled and thinned. The pulling can be made by hand but this requires some practise to yield optimal results and is ideally automated A comparison of the constricted and non-constricted regions of a fused silica capillary is shown in FIGS. 4 and 5. FIGS. 4 and 5 are photomicrographs of a 360-$\mu$m-outer-diameter 150-$\mu$m-inner-diameter fused silica capillary with a 105 $\mu$m wall thickness FIG. 4 shows the central portion of the capillary in FIG. 5 after it has been pulled in a butane/oxygen flame. The polyimide layer that covers the fused silica capillary is burnt off during the pulling process. Thus, a region transparent to light in the wavelength range of about 200–1500 nm is obtained. The inner diameter is now about 8 $\mu$m and the outer diameter is about 18 $\mu$m and the wall thickness about 5 $\mu$m. A more detailed account on optimal capillary dimensions for single-molecule detection is given in the appended examples.

Figure 6:
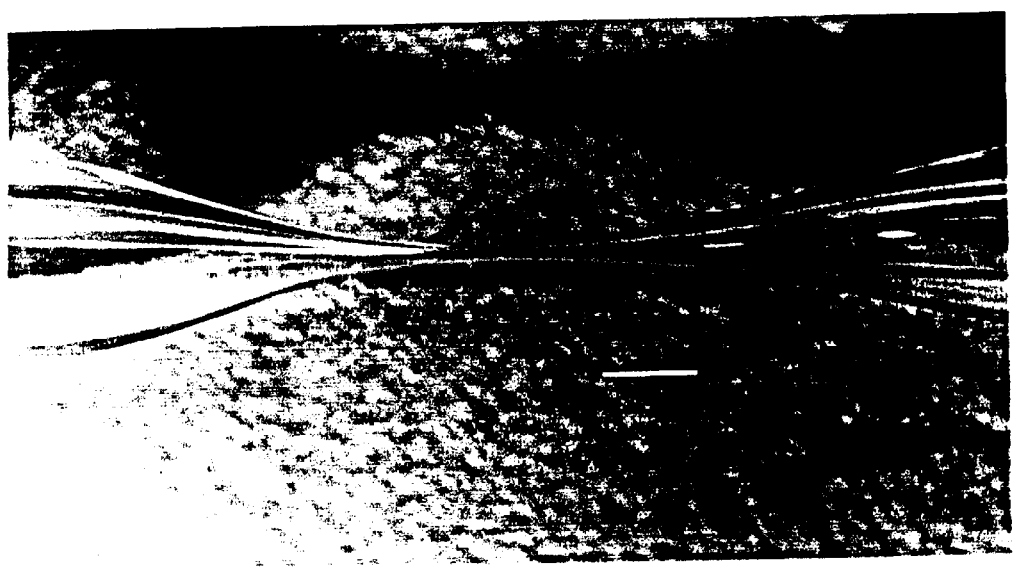
FIG. 6 is a photomicrograph of a glass capillary that has been pulled using a heated filament; the scale bar is about 300 $\mu$m.

It is more preferred to pull the capillary by more controlled techniques. These techniques include pulling of capillaries where an ultra-small section of the capillary is heated using a filament or a $CO_2$ laser. The pulling force is carefully applied through electronic actuators, mechanical manipulators or weight, FIG. 6 shows a photomicrograph of a glass capillary that has been pulled using a heated filament. The scale bar is about 300 $\mu$m. The outer diameter of the constricted region is about 50 $\mu$m and the inner diameter is about 10 $\mu$m.

In order to strengthen the mechanical stability of the capillary, the pulled region may be coated on the outside with a transparent polymeric material. A non-limiting example of such a polymer is PDMS.

Constricted regions can also be obtained by etching with hydrofluoric acid, or by drilling in a lathe. However, this technique does not decrease the inner diameter of the capillaries, which is a drawback. Separation channels can also be manufactured using nanolithography on chip materials, such as silicon or glass.

If commercial fused silica capillaries are used in the production of the flow cells according to the invention it is often necessary to modify the inner surface of the channel structure. Most commercial glass capillaries are coated with a polyimide layer to improve their mechanical stability. In order to focus a laser in the interiors of such capillaries, the polyimide layer needs to be removed, which otherwise blocks the laser light. In the pulling process when using heated filaments, or flames, this polyimide layer is removed. Following pulling, the area needs to be cleaned thoroughly with dichloromethane, or any other solvent of choice to remove soot particles.

Since the present invention aims at applications where only trace amounts of materials are present, it is of utmost importance that the analytes do not adhere to the capillary walls, which contains charged silanol groups. Therefore, in particular, for the analysis of positively charged materials, it is important to coat the interior walls of the capillaries with a strongly hydrophobic film. For example, Sigmacoat, Sylgard, or other silanising agents can be used for this purpose.

Figure 7:
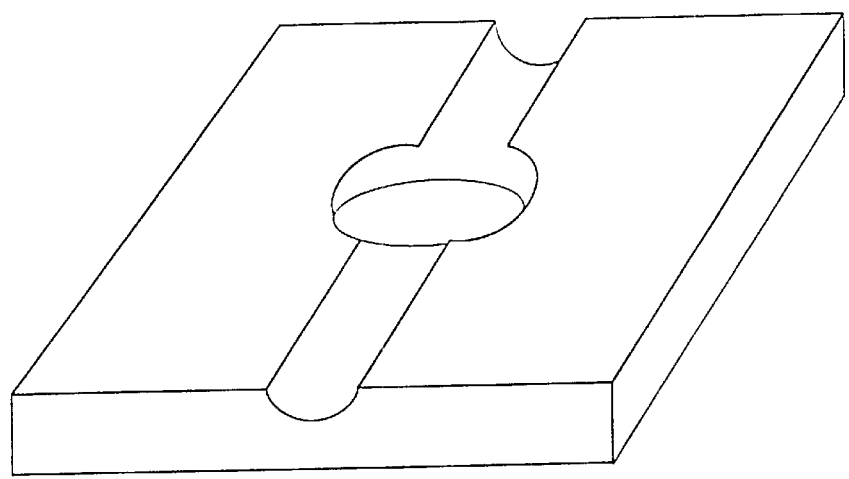
FIG. 7 shows a holder suitable for the flow cell according to the invention.
Figure 8:
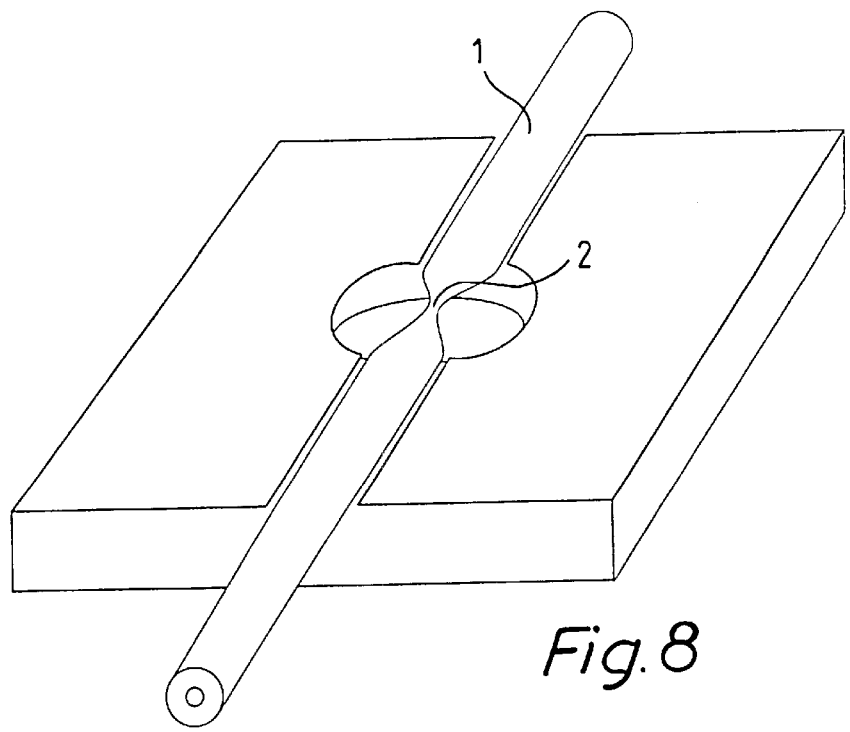
FIG. 8 shows the holder of FIG. 7 with a mounted flow cell.

Once the flow cell is constructed, it is preferably mounted immediately on a capillary holder to minimise movement of the thin-walled constricted region of the capillary. An example of a suitable holder for use in combination with a microscope is shown in FIG. 7. The holder is then mounted onto a microscope stage and serves to immobilise the capillary The size of the capillary is preferably roughly the size of a microscope cover slip (60×25 mm) and the thickness is made to match the size of the capillaries (about 0.5 mm to 2.5 mm). Grooves matching the outer diameter of the non-constricted region of the capillary are etched or drilled into the substrate as shown in the figure. The size of the hole in the middle of the holder is chosen to accommodate the desired type of lens that focuses the laser light onto the capillary. The same holder with a mounted flow cell is shown in FIG. 8. The capillary can be immobilised using glue or adhesive tape. The constricted region of the capillary is positioned in the hole to allow laser light entering the capillary at that region.

If the constricted region is not extremely thin and fragile, the capillary can be pulled first, as discussed above, and then mounted onto the holder for immobilisation. For a constricted region that is thin and extremely fragile, it is best to avoid transfer of the fragile pulled capillary onto the holder after construction. It is preferable to first mount an unpulled flow cell capillary in the holder, and the constricted region subsequently fabricated from this holder-mounted capillary. Therefore, the preferred procedure is to first thread the flow-cell capillary through tie openings of the holder's two capillary conduits. The two capillary conduits are placed such that the region of the flow-cell capillary above the holder opening is exposed and is not surrounded by the conduits. This is the region that the constricted region of the capillary, once constructed, will reside. To provide the best support for the constricted region, the inner diameter of the capillary conduits should match the outer diameter of the capillary. Once the flow-cell capillary is in place, heat (e.g. a flame or $CO_2$ laser pulses) is applied through the holder's opening to the exposed region of the capillary. And when the melting temperature of the capillary is reached, force is applied to pull and thin the capillary to form the constricted region. After the constricted region is fabricated, this constricted region can then be centred above the holder opening by gently sliding the capillary along the capillary conduits. If necessary, adhesives might be used subsequently to further immobilise the constricted region onto the holder.

The holder is preferably made of a material suitable for use in combination with e.g. oil or water immersion optics, and for that purpose it should also be able to accommodate oil or water. The material may e.g. be glass or plastic material such as polycarbonate.

For detection according to the invention, the constricted region of the flow cell according to the invention is illuminated by a light beam. Preferably, this beam is a laser beam. This is illustrated in FIG. 9. The beam 3 from the light source 4 is, by means of a high-numerical aperture microscope objective 5 focused close to or at the diffraction limit inside the constricted region 2. The light for excitation of fluorescent species inside the constricted region of a capillary is ideally provided by a laser source. Since laser light is of a coherent nature, i.e. all photons have the same frequency, phase, and direction and low divergence, it can be brought to a diffraction-limited spot with high quality optics The beam waist of a tightly focused laser in the $TEM_{00}$ mode can be about 500 nm to a few micrometers and has a Gaussian intensity distribution, as shown in FIG. 10, which illustrates a cross sectional view of an idealised laser beam brought to the limit of diffraction. By matching the size of the constricted region of the capillary to the size of a tightly focused, ideally a diffraction limited laser spot, which is illustrated in FIG. 11, detection of single fluorescent species in the probe volume can be obtained at a high signal-to-noise-ratio. Basically this is because scattering from Rayleigh and Raman processes are minimised. Because of the size-matching between the tightly focused laser spot and the capillary, the probability of detecting a molecule is close to unity. The laser is focused close to or at the diffraction limit. Immersion oil or water is used between the objective and the capillary in order to achieve a tight focusing. Focusing of the laser light onto the capillary is best achieved by using a 100×high numerical aperture (about 1.3–1.4) microscope oil or water immersion objective. Immersion oil or water is preferably used between the objective and the capillary in order to achieve a tight focusing, this is, however, left out in the figure for clarity reasons. Due to the fact that oil or water immersion optics are used, and the fact that the capillary walls at the constricted region are extremely thin, minimal distortion of the laser focus is obtained. This is an extremely important characteristic of the system.

Figure 12:
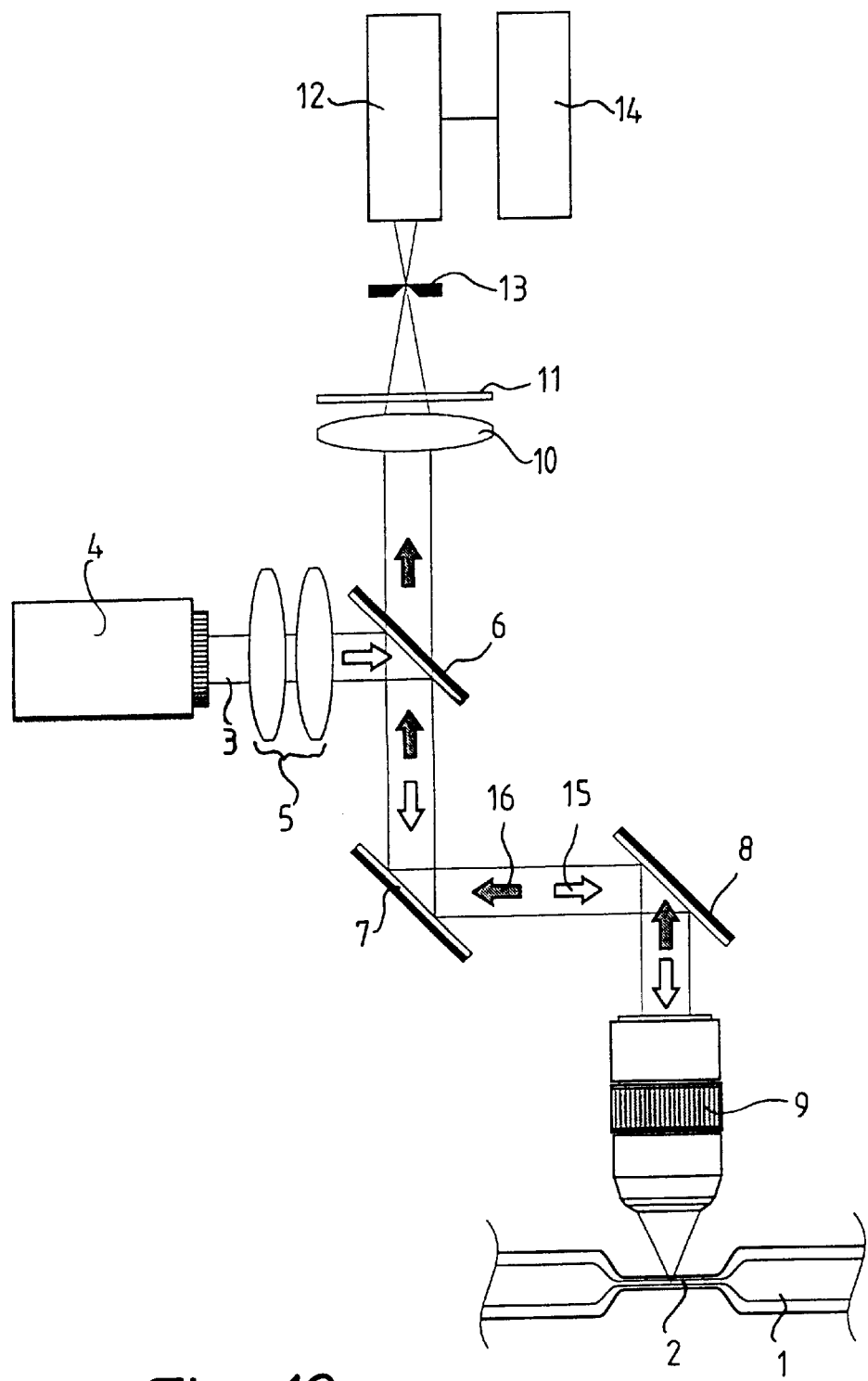
FIG. 12 shows a confocal optical arrangement used in a preferred embodiment of the invention.

The preferred embodiment of the invention is shown in FIG. 12. In the preferred embodiment a confocal optical arrangement is used for detection of fluorescent molecules inside the constricted region 2 of the channel structure 1. The laser light is sent through a telescope 5 that is used to achieve an appropriate laser beam diameter. A dichroic mirror 6 and two mirrors 7, 8 are arranged between the laser source 4 and a microscope objective 9, which focuses the laser beam inside the constricted region 2 of the channel structure 1. The fluorescence light passes from the objective 9, through a lens 10 and a filter 11 to the detector 12. Detection is made through a pinhole or slit 13 which serves to spatially reject the out-of-plane light. A highly sensitive photon detector 12, such as a single photon counting diode, or a photon counting photomultiplier tube is preferably used for detection. The detecting unit 12 may be coupled to for example a multi-channel scaler and a computer 14 to facilitate the data collection.

The set-up is ideally mounted onto a microscope.

In the figure, laser light exciting the fluorescent molecules is represented as open arrows 15, and fluorescent light from excited molecules is represented by filled arrows 16. As before oil or water immersion is preferably used between the microscope objective 9 and the constricted region of the capillary, however, this has been left out in the figure for clarity reasons.

Figure 13:
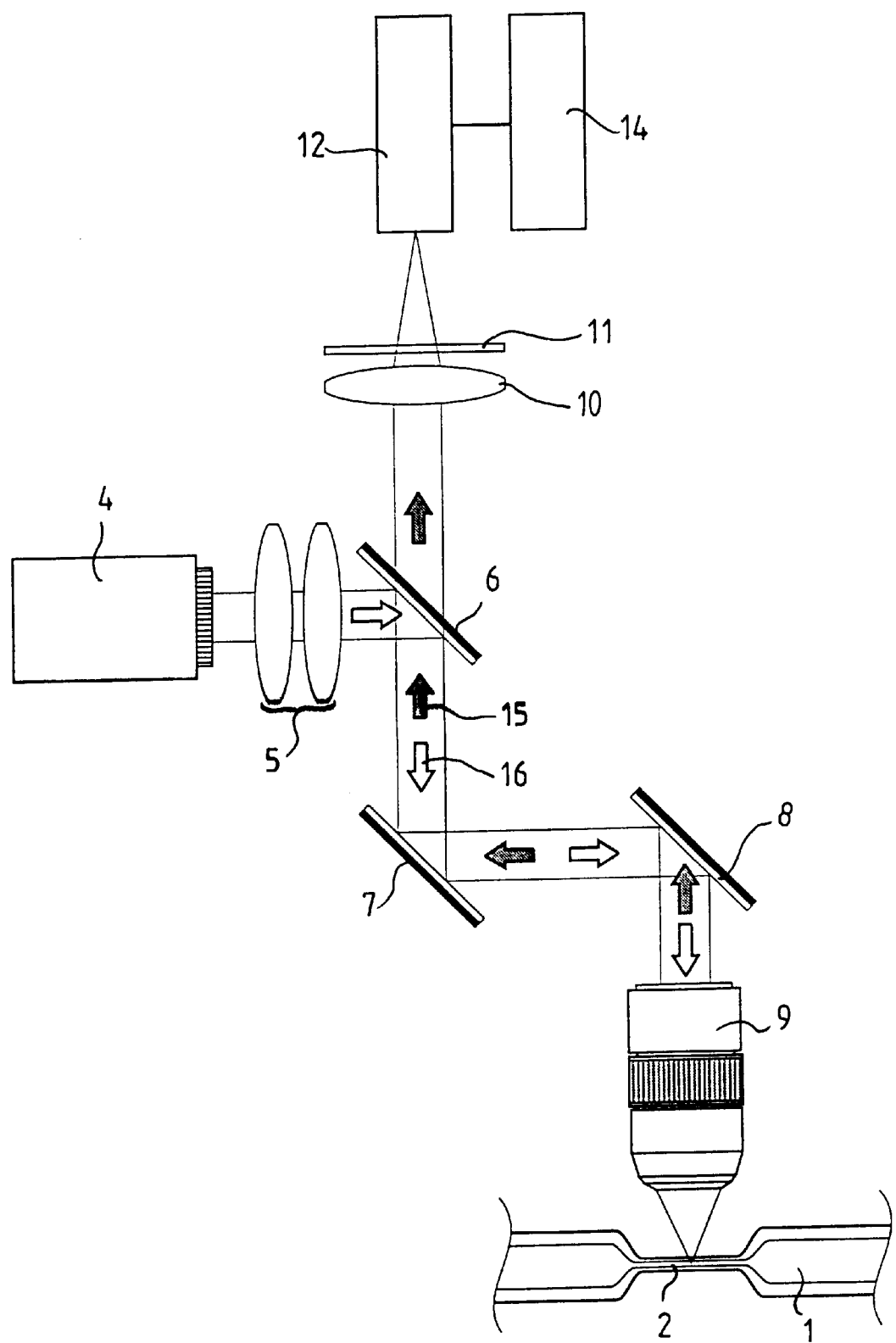
FIG. 13 shows a non-confocal optical arrangement used in another preferred embodiment of the invention.

According to the invention it is also possible to use a non-confocal detection mode. A preferred embodiment of this variant is shown in FIG. 13. In the nonconfocal detection mode detection is no longer made through a pinhole or slit. The set-up with the laser source 4, telescope 5, dichroic mirror 6, mirrors 7, 8, lens 10, filter 11, microscope objective 9, channel structure 1 and constricted region 2 resembles the embodiment described in FIG. 12. In this embodiment detection is preferably made by use of a photon counting diode, a highly sensitive photon counting charge coupled device 12, or a VIM camera or a streak camera. As before, the detecting unit 12 may be coupled to for example a multi-channel scaler and a computer 14 to facilitate the data collection.

Excitation of the fluorophores is ideally achieved by two- or multi-photon processes. The set-up is ideally mounted onto a microscope.

Figure 14:
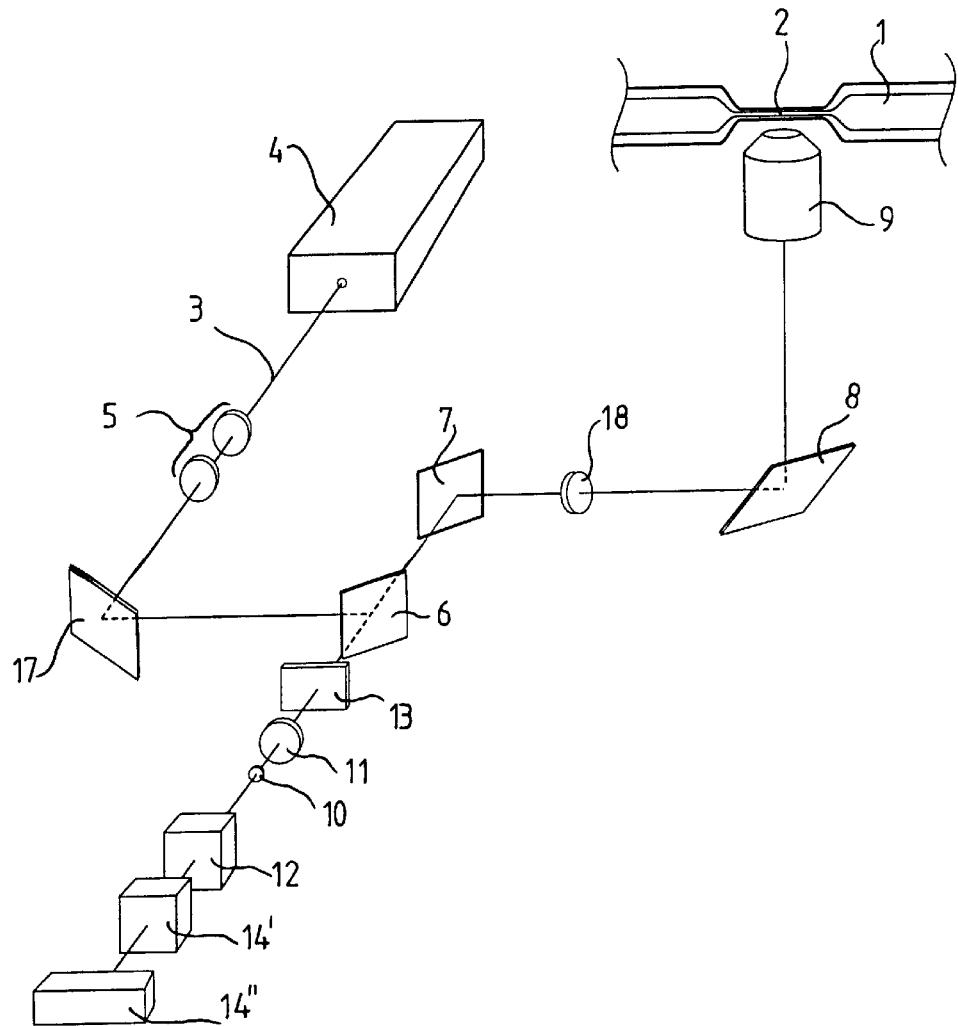
FIG. 14 shows the most preferred embodiment of the invention in which a scanning confocal fluorescence microscope (SCFM) is used.

As in FIG. 12, laser light is represented as open arrows 15, the fluorescent light is represented by filled arrows 16, and the oil or water immersion used between the microscope objective and the constricted region of the capillary is left out for clarity reasons The most preferred embodiment of the invention in which a scanning confocal fluorescence microscope (SCFM) is used, is illustrated in FIG. 14. The beam 3 from the laser 4, preferably an argon laser, is first sent through a telescope 5, and is then reflected off a mirror 17 onto a dichroic beam-splitter 6. The reflected laser light from the dichroic mirror 6 then hits a scanning mirror 7. The angle displacement of this mirror is the fourier transform pair of the distance displacement of the laser focus at the object planer In this way, the object plane can be scanned by displacing the angles of the scanning mirror. After reflecting from the scanning mirror 7, the laser beam passes through a relay lens 18 and is reflected off a mirror 8 that resides inside the microscope. The reflected laser light enters a high numerical aperture objective 9 (100×, N.A.=1.4) and is then focused to illuminate the constricted region 2 of the capillary channel 1 for laser-induced fluorescence: The capillary 1 or at least the constricted region thereof 2 is immersed in oil or water for better refractive index matching.

The emitted fluorescence is collected by the objective 9 and directed onto a detector 12. After reflecting from the scanning mirror 7, the fluorescence light passes through the dichroic beam-splitter 6 and encounters a pinhole 13. (25 to 150 μm in diameter), which is placed at the conjugate image plane. This pinhole 13 provides the depth discrimination that characterises a confocal microscope After the pinhole, the collected fluorescence is spectrally filtered by a bandpass filter 11, which ensures that only photons that fall inside the emission spectrum of the fluorophore Are sent to the detector 12. This filtered signal is subsequently focused by a lens 10 onto a high-sensitivity single-photon counting detector As 12. The detected signals are collected and displayed by a multi-channel scaler 14' connected to a computer 14".

Figure 15:
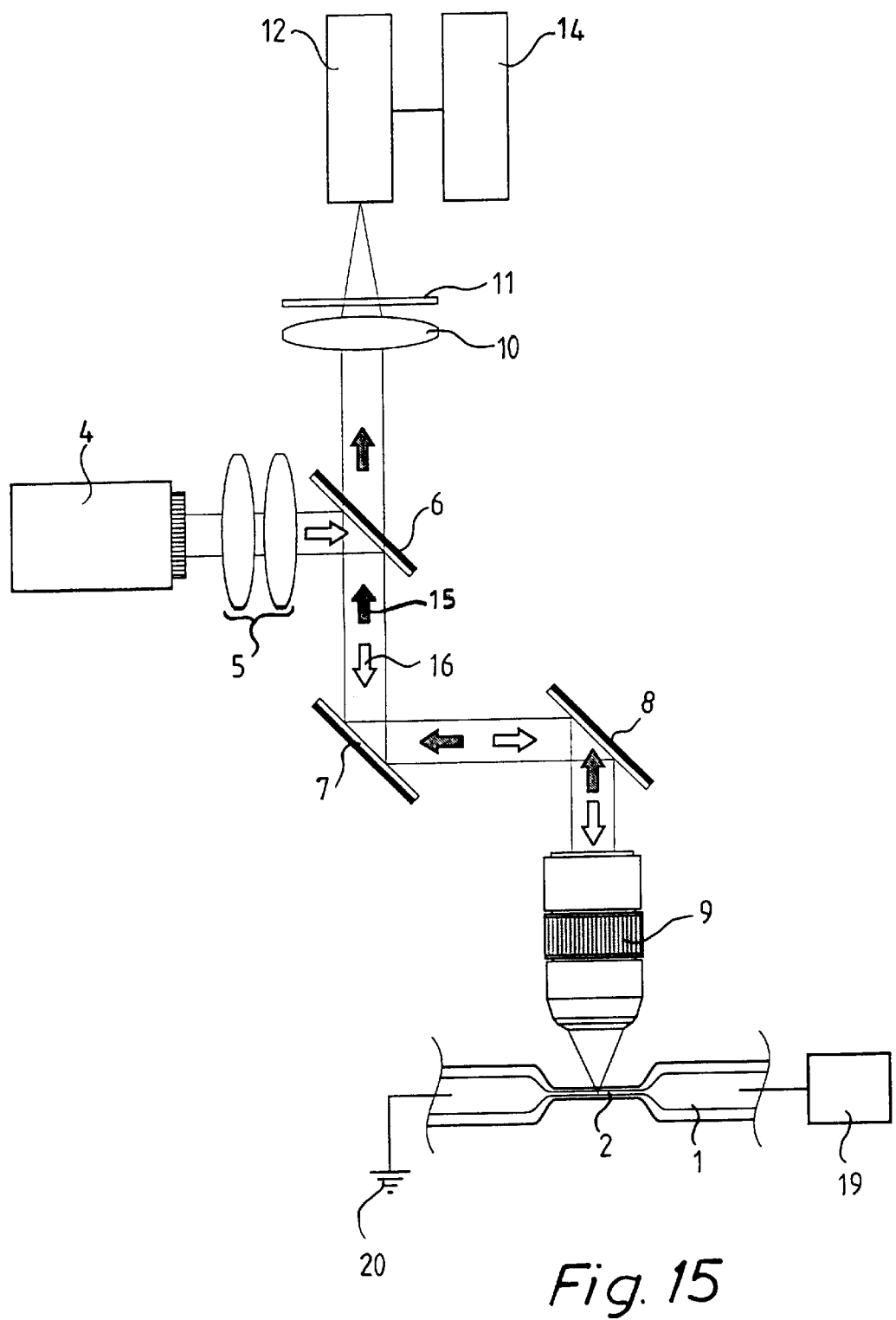
FIG. 15 illustrates use of the flow cell according to the invention as an integrated separation and detection device.

The preferred embodiment of the invention for use as an integrated separation and detection device is shown in FIG. 15; The beam from a laser source 4 is focused by a high numerical aperture microscope objective 9 onto the constricted region 2 of a capillary 1. An oil or water immersion (not shown) is preferably used between the microscope objective 9 and the constricted region 2 of the capillary 1. The detection mode shown in the figure is a non-confocal arrangement but can of course be a confocal arrangement. The capillary 1 can be used as the channel for electrophoretic separations by connecting one end of the capillary to a high voltage power supply 19 (usually the sample inlet end of the capillary) and one end to ground 20 (usually the capillary outlet end). Fluorescent molecules that are separated electrophoretically, i.e. on the basis of their charge-to-frictional drag ratio, are detected in the constricted region 2.

In a similar way, the flow cell can be used for e.g. capillary electrochromatography, liquid chromatography, gas chromatography, or flow injection analysis.

The invention will now be further explained in the following examples. These examples are only intended to illustrate the invention and should in no way be considered to limit the scope of the invention.

EXAMPLE 1

Detection of Individual 30-nm Fluorescent Beads in a Pulled Capillary by Scanning Confocal Fluorescence Microscope (SCFM)

The optical set-up used in this example is the preferred embodiment illustrated in 14, which has been described above. The sample analysed in different ways in this example was a disperse solution of latex beads with a diameter of approximately 30 nm, containing an equivalent of approximately 100 fluorescein molecules (Molecular Probes, Eugene, OR, U.S.A.). Three experiments were made, wherein detection was performed in three different ways; in a regular capillary, in a pulled capillary with a constricted region according to the invention and in a drop on a coverslip.

Figure 16:
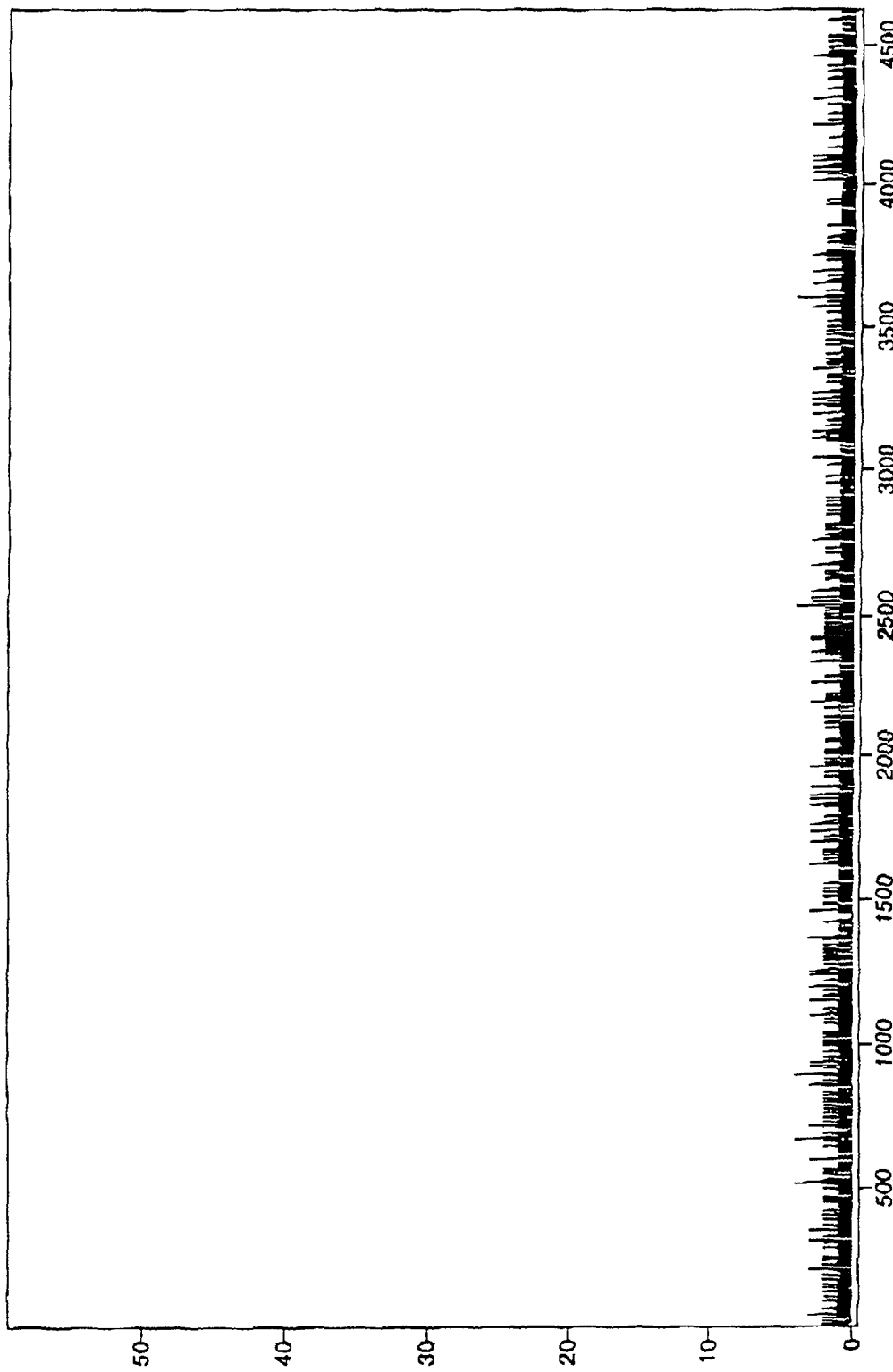
FIG. 16 shows the result of detection of fluorescent latex beads in a regular 360 $\mu$m-outer-diameter 150 $\mu$m-inner-diameter fused silica capillary with a 105 $\mu$m wall thickness, it is not possible to detect any fluorescence signal from the beads over the background noise.

Experiment 1:

The result of detection of the fluorescent beads in a regular 360 $\mu$m-outer-diameter 150 $\mu$m-inner-diameter fused silica capillary with a 105 $\mu$m wall thickness is shown in FIG. 16. The capillary used in this first experiment did not comprise any constricted regions. The capillary wall therefore dramatically distorts the excitation laser beam, which in turn results in significant distortions of the laser focus. Since the capillary wall has a cylindrical symmetry, it acts as a cylindrical lens that strongly focuses the laser beam along one dimension. This cylindrical distortion is the main cause of the observed spherical aberration in this system. Spherical aberration is detrimental to the performance of a confocal microscope. It is clear from the figure that it is not possible to detect any fluorescence signal from the beads over the background noise in this configuration.

Figure 17:
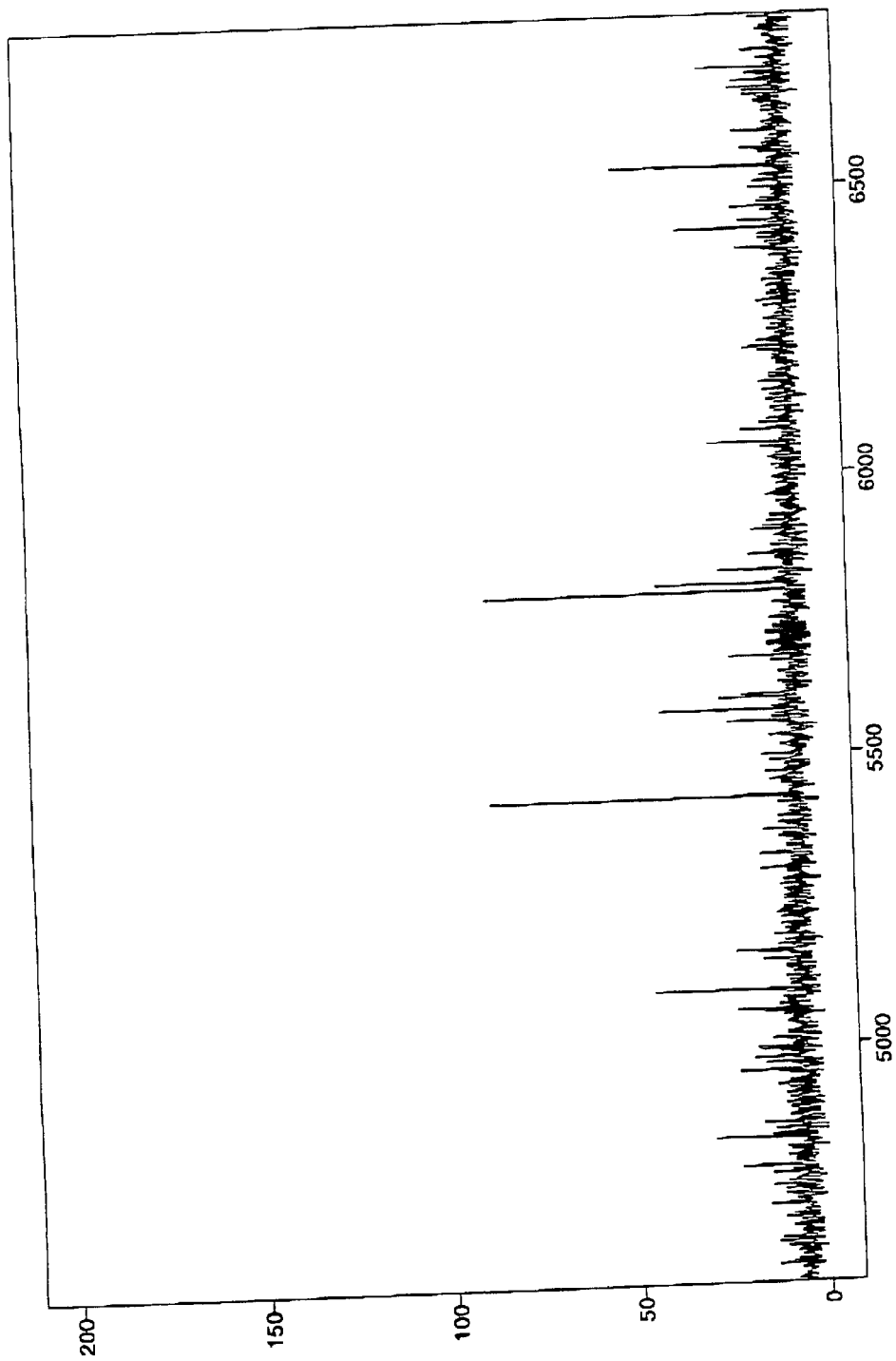
FIG. 17 shows detection of fluorescent latex beads during a 3 second detection period in a pulled capillary with an inner diameter of about 8 $\mu$m and an outer diameter of about 18 $\mu$m and a wall thickness of about 5 $\mu$m; where each peak in most cases signals the presence of a single bead.

Experiment 2:

The result from detection according to the invention is shown in FIG. 17. The detection of the fluorescent beads was performed during a 3 second detection period in a capillary similar to the one used in the first experiment, except for the fact that it comprised a constricted region with an inner diameter of about 8 $\mu$m, an outer diameter of about 18 $\mu$m, and thus a wall thickness of about 5 $\mu$m. This 20-times reduction of wall thickness is crucial to maintaining a good quality laser focus for detection with SCFM. Although the presence of the capillary still introduces spherical aberration, the extent of this aberration is dramatically reduced. At the limit where the dimensions of the pulled capillary is comparable to that of the laser focus (about 1 or 2 $\mu$m), spherical aberration introduced by the capillary would become negligible. The signal collected from this constricted region of the capillary demonstrates that individual beads can be detected with good signal to noise ratio. In addition, since the channel dimension is physically reduced, analytes travelling down the capillary are forced to enter the laser probe volume to register their presence. Consequently, the sampling efficiency (percentage of molecules crossing the probe volume) should be 100 % for this type of system. Each peak in FIG. 17, in most cases, signals the presence of a single bead.

Figure 18:
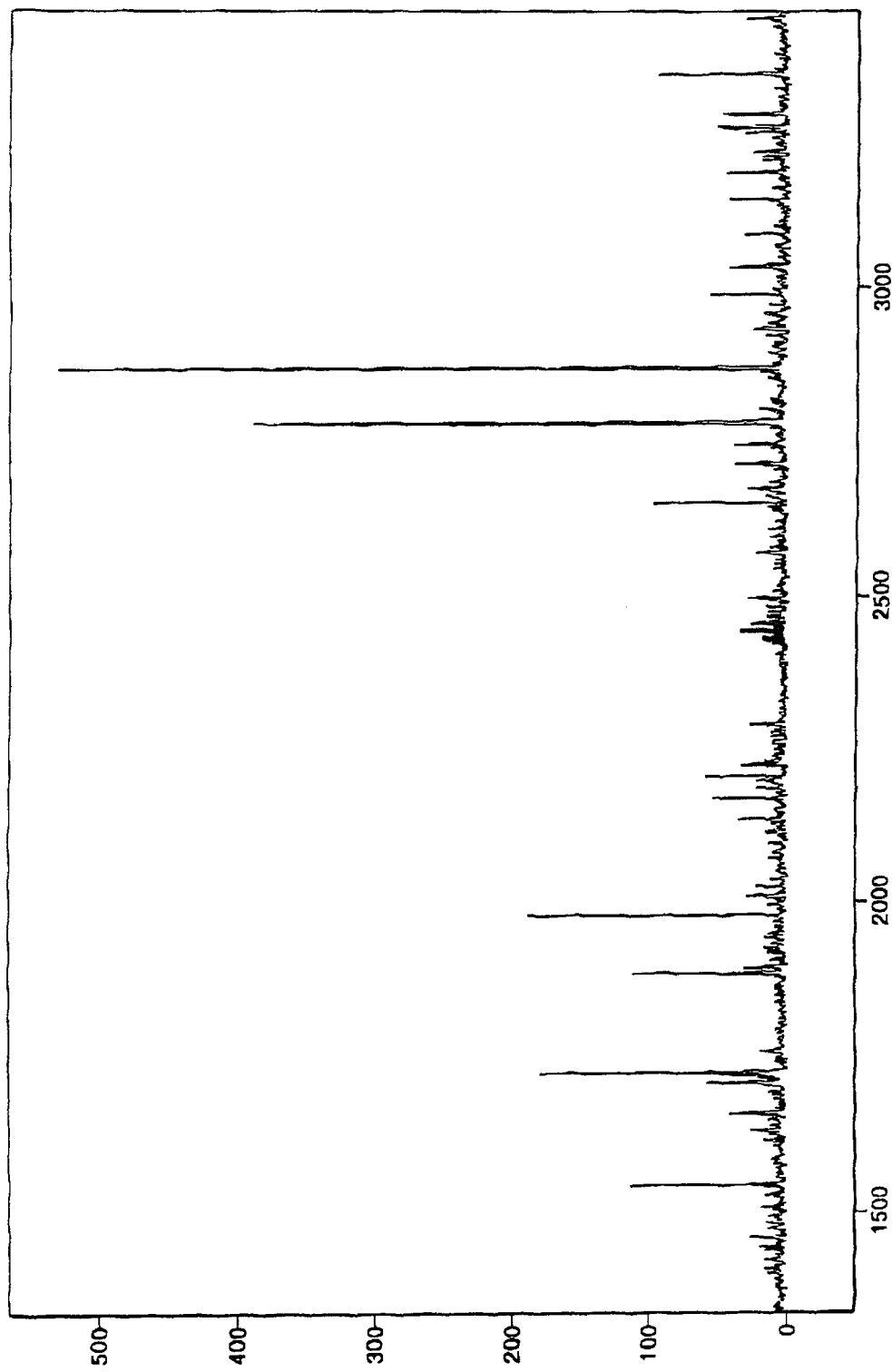
FIG. 18 shows detection of fluorescent latex beads during a 4 second recording time; detection was performed in a drop containing the beads placed on a coverslip.

Experiment 3:

The result from detection of the fluoresceinated beads in a drop containing the beads placed on a coverslip is shown in FIG. 18. Detection was made during a 4 second recording time In this case, there is no capillary present to distort the laser focus. Under this condition, even a single fluorescent molecule, such as fluorescein, can be detected with a good signal-to-noise ratio. The collected fluorescence signal shown in the figure is indeed better than that obtained inside a pulled capillary channel. However, it is not possible to ensure detection of all fluoresceinated beads present in the drop.

The signal-to-noise ratio achieved in experiment 2, wherein the pulled capillary was used, is preliminary and can be easily improved with a better controlled capillary pulling process and optimal capillary dimensions. In this experiment, the capillary was heated by a butane flame and the pulling force applied by hand in order to produce the constricted region. A pulled channel of much better quality could be achieved with a controlled heating source, such as a $CO_2$ laser, and with a carefully controlled pulling force, as through mechanical manipulators or electronically controlled actuators. The SCFM detection system can also be optimised for detection of fluorophores inside a pulled capillary channel rather than on a coverslip. With these improvements, single molecules can be detected with good signal-to-noise ratios inside a capillary.

In addition, the current SCFM detection scheme makes use of a scanning mirror that can be adapted for rapidly (milliseconds) scanning and collecting signals from a large parallel array of capillaries. This will prove especially significant in applications that involve screening where high throughput is necessary.

EXAMPLE 2

Figure 19:
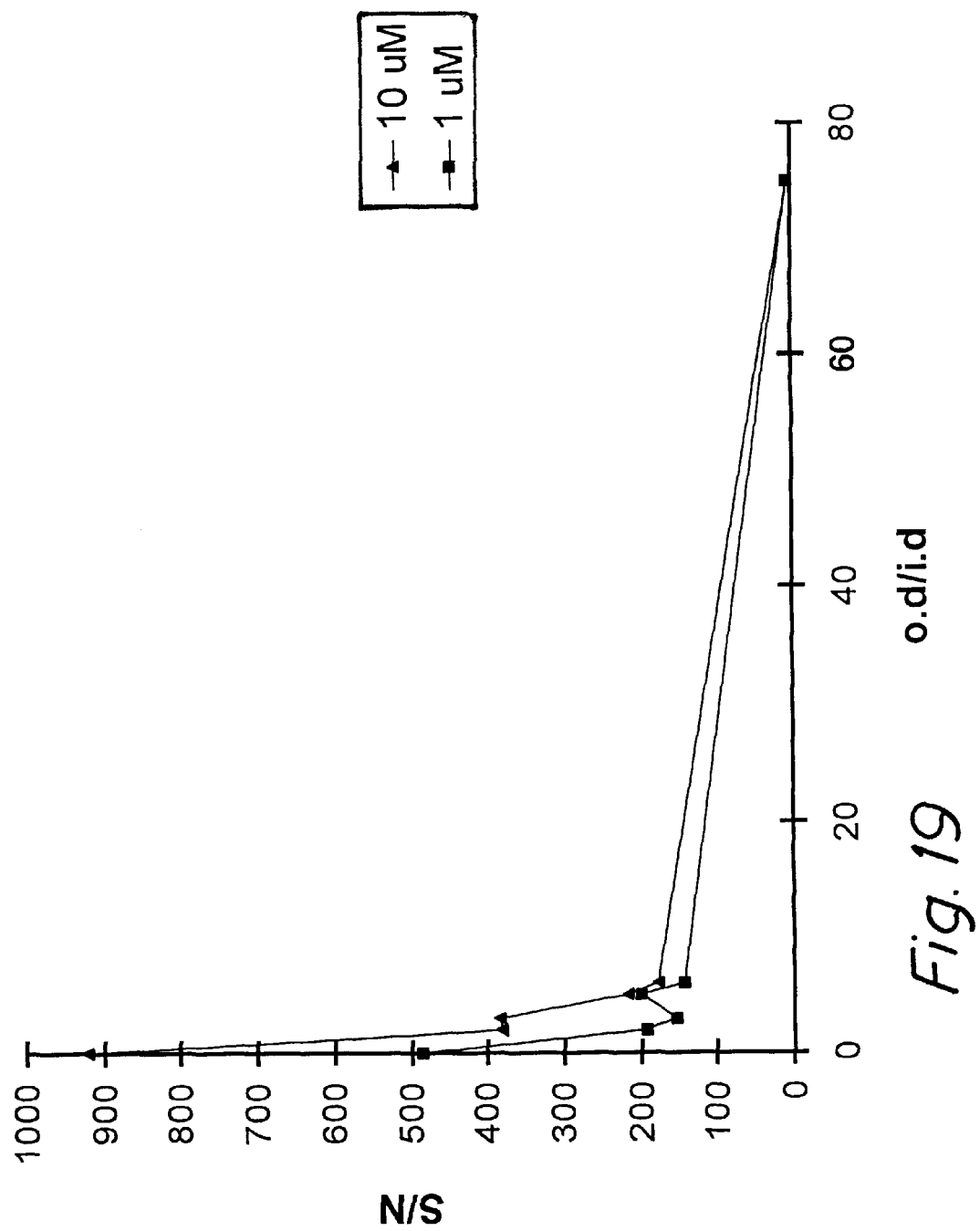
FIG. 19 shows how the signal-to-noise ratio depends on capillary dimensions; the signal from a streaming solution of laser-excited fluorescein through the capillary is compared with the signal from pure milliQ water.

In FIG. 19 is shown the result from comparing the signal-to-noise ratio in different capillary-dimensions. A laser beam is focused inside a fused silica capillary to excite fluorophores in a solution. The fluorescence signal from a streaming solution of fluorescein through the capillary is compared with the signal from pure milliQ water. The fluorescein solution also contained NaOH (10 mM) and β-mercaptoethanol (1 % v/v) for optimal fluorescence condition. The fused silica capillaries used are from Polymicro Technologies, Phoenix, Ariz., with an outer diameter of 150 $\mu$m. The inner diameter were 2 $\mu$m, 10 $\mu$m, 25 $\mu$m, 50 $\mu$m and 75 $\mu$m, respectively. All capillaries were cut in 15 cm length and about one centimeter of the protection film of polyimide was burned away to create a detection window. The capillaries were coupled to a syringe pump by plastic tubings to force the solution through. The fluorescent solution contained fluorescein (10 $\mu$M (filled triangles) or 1 $\mu$M (filled squares) from Sigma-Aldrich, St. Louis, Mo.), NaOH (10 mM from Eka Nobel, Stenungsund, Sweden) and β-mercaptoethanol (1 % v/v from Sigma-Aldrich, St. Louis, Mo.) to obtain a optimal fluorescence with minimal photobleaching. The 488 nm line from an Ar+laser (Spectra-Physics 2025-05, Mountain View, Calif., USA) is sent through a neutral density filter (Newport ND 20, Irvine, Calif., USA), collected and focused by a spherical lens (Newport, Irvine; Calif., USA) to at last be reflected into the microscope (Leica DM IRB, Wetzlar, Germany) by a dichroic mirror (Newport, Irvine, Calif., USA). Inside the microscope there is a polychroic mirror (Omega Optical, Inc., Brattleboro, Vt., USA) which sent the light through the objective (Leica PL Fluotar 100×, N.A.=1.3, oil immersion) to excite the molecules. The fluorescence light passes back from the objective, through a 50 $\mu$m pinhole (Melles Griot, Irvine, Calif., USA) which serves to spatially reject the out-of-plane light. The fluorescence from the image plane is sent through a bandpass filter Chroma Technology Corp. HQ 525/50, Brattleboro, Vt., USA) and a spherical lens (Newport, Irvine, Calif., USA) focused the light onto a highly sensitive single photon counting module (EG&G Ortec, Oak Ridge, Tenn., USA). The pinhole, the spherical lens and the detector are mounted on three-dimensional translation stages (Newport, Irvine, Calif., USA) to make it possible to move them independently. The detecting unit is coupled to a multi-channel scaler (EG&G Ortec, Oak Ridge, Tenn., USA) and a computer to facilitate the data collection.

This is done for several capillaries with the same outer diameter (150 µm), but with different inner diameters from 2 µm to 75 µm. The signal-to-noise ratios from the capillaries are also compared with the ratio from a fluorescein solution placed on a cover slip (o.d/i.d equal to zero). Detection was made during a 6 second recording time.

It is obvious from these plots that the capillary with the thickest walls (highest o.d/i.d ratio) shows the lowest signal-to-noise ratio because the laser focus is distorted the most from cylindrical lensing action, resulting in optical aberrations. The capillaries with thinner walls do not display such effects to the same extent and the signal-to-noise ratios are therefore much better. With a capillary of an i.d. of about the size of the diffraction-limited laser focus, and an outer diameter a factor 1.5 to 5 times of said size of the diffraction-limited laser focus would result in optimal detection conditions.

What is claimed is:

1. An optical method for detection of fluorescent molecules based on the use of a focused light beam and light-induced fluorescence spectroscopy, said method comprising the steps of:
   causing a sample potentially having at least one fluorescent molecule to flow through at least one flow cell, said flow cell including at least one channel structure, said channel structure comprising at least one constricted region, said at least one constricted region having a cross-section of a dimension corresponding to the size of a focused light spot near a diffraction limit of said focused light and transparent walls;
   focusing at least one light beam to be at or near its diffraction limit at said at least one constricted region to thereby excite any fluorescent molecules present in the sample passing through said at least one constricted region; and
   detecting fluorescence emitted when a fluorescent molecule or a group of molecules passes through said at least one constricted region and is excited by said at least one focused light beam.

2. A method according to claim 1, wherein said at least one light beam is a laser beam.

3. A method according to claim 1, wherein the detecting step includes detecting at least one single fluorescent molecule or a particle with a conservative number of fluorophores.

4. A method according to claim 3, further comprising determining the concentration of said molecules or particles in said sample without the use of external or internal standards.

5. A method according to claim 1, further comprising placing said at least one constricted region of the flow cell in a medium having a refractive index close to that of the material of said at least one constricted region.

6. A method according to claim 5, wherein said medium is selected from the group consisting of oil and water.

7. A method according to claim 1, wherein the channel structure is a capillary.

8. A method according to claim 7, wherein the capillary is a fused silica glass capillary.

9. A method according to claim 1, wherein the channel structure is a groove etched into a chip.

10. A method according to claim 1, wherein said at least one constricted region has an inner diameter in the range of approximately 0.2–8 µm and an outer diameter in the range of approximately 0.4–40 µm.

11. A method according to claim 10, wherein said at least one constricted region has an inner diameter in the range of 1–2 µm and an outer diameter less than or equal to five (5) times the inner diameter.

12. A method according to claim 1, wherein said at least one light beam is provided by an argon ion laser.

13. A method according to claim 1, wherein the wavelength of the light beam used is in the range of approximately 200 and 1500 nm.

14. A method according to claim 1, wherein said detection step includes detection through use of a photon detector.

15. A method according to claim 1, wherein said detection step includes detection through use of a photon detector selected from a group consisting of a single photon counting diode, or a photon counting photomultiplier tube, a highly sensitive photon counting charge coupled device, a VIM camera, and a streak camera.

16. A method according to claim 1, wherein said detection step includes detection at a single wavelength.

17. A method according to claim 1, wherein said detection step includes detection in a multicolour format.

18. A method according to claim 1, wherein said detection step includes detection in a confocal mode.

19. A method according to claim 1, wherein said focusing step includes focusing light from more than one light source, each light source emitting light at a different wavelength.

20. A method according to claim 1, wherein detection step includes detection at more than one constricted region for cross-correlation of the data.

21. A method according to claim 1, wherein said focusing step includes a two-photon or a multi-photon mode excitation for the excitation of the fluorescent molecules.

22. An apparatus for detection of fluorescent molecules, said apparatus comprising:
   at least one light source;
   at least one fluorescence detector; and
   at least one flow cell, said flow cell including
      at least one channel structure comprising
         at least one constricted region,
   wherein said at least one constricted region has a cross-section of a dimension corresponding to the size of a focused light spot at or near the diffraction limit of a light beam from said light source and transparent walls, and further wherein an outer diameter of said constricted region is no more than ten (10) times as large than that of said focused light spot.

23. An apparatus according to claim 22, wherein said at least one light source is a laser source.

24. An apparatus according to claim 22, further comprising means for focusing the light beam from the light source to be near the diffraction limit inside said constricted region.

25. An apparatus according to claim 24, wherein said means for focusing of the light beam includes a high-numerical aperture microscope objective.

26. An apparatus according to claim 24, further comprising a medium with a refractive index close to that of the material of said at least one constricted region of the channel structure arranged between said means for focusing and said at least one constricted region.

27. An apparatus according to claim 26, wherein said medium is selected from the group consisting of oil and water.

28. An apparatus according to claim 22, wherein the channel structure is a capillary.

29. An apparatus according to claim 28, wherein the capillary is a fused silica glass capillary.

30. An apparatus according to claim 22, wherein the channel structure is a groove etched into a chip.

31. An apparatus according to claim 22, wherein said at least one constricted region has an inner diameter of approximately 0.2–8 µm and an outer diameter of approximately 0.4–40 µm.

32. An apparatus according to claim 22, wherein said at least one constricted region has an inner diameter in the range of 1–2 µm and an outer diameter less than or equal to five (5) times the inner diameter.

33. An apparatus according to claim 22, wherein the light source is an argon ion laser.

34. An apparatus according to claim 22, wherein said at least one fluorescence detector is photon detector.

35. An apparatus according to claim 30, wherein said at least one fluorescence detector is a photon detector selected from a group consisting of: a single photon counting diode, a photon counting photomultiplier tube, a highly sensitive photon counting charge coupled device, a VIM camera, and a streak camera.

36. An apparatus according to claim 22, wherein the detector uses confocal detection.

37. An apparatus according to claim 22, wherein said flow channel forms an integrated and continuous part of a flow injection analysis system or a separation system.

38. An apparatus according to claim 37, further comprising system selected from the group consisting of a capillary electrophoresis, capillary electrochromatography, liquid chromatography, or gas chromatography system, wherein said flow channel forms an integrated and continuous part of said system.

* * * * *